(12) United States Patent
Bernaert et al.

(10) Patent No.: US 8,709,503 B2
(45) Date of Patent: Apr. 29, 2014

(54) USE OF COCOA EXTRACT

(75) Inventors: Herwig Bernaert, Lebbeke-Wieze (BE); Leen Allegaert, Lebbeke-Wieze (BE)

(73) Assignee: Barry Callebaut AG, Zurich (CH)

( * ) Notice: Subject to any disclaimer, the term of this patent is extended or adjusted under 35 U.S.C. 154(b) by 36 days.

(21) Appl. No.: 12/597,569

(22) PCT Filed: Apr. 24, 2008

(86) PCT No.: PCT/EP2008/003322
§ 371 (c)(1),
(2), (4) Date: Feb. 2, 2010

(87) PCT Pub. No.: WO2008/131910
PCT Pub. Date: Nov. 6, 2008

(65) Prior Publication Data
US 2010/0130422 A1    May 27, 2010

Related U.S. Application Data

(60) Provisional application No. 60/926,328, filed on Apr. 26, 2007.

(30) Foreign Application Priority Data

Oct. 8, 2007  (GB) .................................. 0719542.3

(51) Int. Cl.
*A61K 36/00* (2006.01)

(52) U.S. Cl.
USPC ......................................................... 424/725

(58) Field of Classification Search
None
See application file for complete search history.

(56) References Cited

U.S. PATENT DOCUMENTS

| | | | |
|---|---|---|---|
| 4,288,433 A | 9/1981 | Koulbanis et al. | |
| 5,338,554 A | 8/1994 | Vogt et al. | |
| 5,543,415 A | 8/1996 | Suzuki et al. | |
| 5,667,793 A | 9/1997 | Cho et al. | |
| 5,709,864 A | 1/1998 | Andre et al. | |
| 6,174,542 B1 | 1/2001 | Hinton et al. | |
| 6,294,190 B1 | 9/2001 | Nakahara et al. | |
| 6,313,128 B1 | 11/2001 | Blanc-Ferras et al. | |
| 6,420,350 B1 | 7/2002 | Fleischner | |
| 6,927,280 B2 | 8/2005 | Kochhar et al. | |
| 7,037,536 B2 | 5/2006 | Makino et al. | |
| 7,115,285 B2 | 10/2006 | McKee et al. | |
| 7,122,574 B2 | 10/2006 | Romanczyk, Jr. et al. | |
| 2001/0041675 A1 | 11/2001 | Jacobs | |
| 2002/0187211 A1 | 12/2002 | Empie et al. | |
| 2002/0192308 A1 | 12/2002 | Mamana | |
| 2003/0170199 A1 | 9/2003 | Leclere | |
| 2003/0206981 A1 | 11/2003 | Lee et al. | |
| 2004/0005347 A1* | 1/2004 | Ter Laak et al. | 424/440 |
| 2004/0028758 A1 | 2/2004 | Park et al. | |
| 2004/0077556 A1* | 4/2004 | Chinery | 514/27 |
| 2004/0096566 A1* | 5/2004 | Lecoupeau et al. | 426/593 |
| 2004/0198754 A1 | 10/2004 | McKee et al. | |
| 2005/0037025 A1 | 2/2005 | Gow et al. | |
| 2005/0164956 A1 | 7/2005 | Schmitz et al. | |
| 2005/0181083 A1 | 8/2005 | Takagaki et al. | |
| 2006/0057228 A1 | 3/2006 | Zheng et al. | |
| 2006/0134230 A1 | 6/2006 | Abraham | |
| 2006/0182825 A1 | 8/2006 | Prasad et al. | |
| 2006/0204599 A1 | 9/2006 | Wheat | |
| 2006/0210653 A1 | 9/2006 | Gardiner et al. | |
| 2006/0281691 A1 | 12/2006 | Blass | |
| 2006/0286183 A1 | 12/2006 | Gardiner et al. | |
| 2007/0104805 A1 | 5/2007 | Udell | |
| 2007/0116840 A1 | 5/2007 | Prakash et al. | |
| 2007/0148107 A1 | 6/2007 | Sies et al. | |
| 2007/0160690 A1 | 7/2007 | Shell et al. | |
| 2007/0160698 A1 | 7/2007 | Waga et al. | |
| 2007/0178176 A1 | 8/2007 | Kandaswami et al. | |
| 2008/0038290 A1 | 2/2008 | Renimel et al. | |
| 2008/0161386 A1 | 7/2008 | French et al. | |
| 2010/0184666 A1 | 7/2010 | Bernaert et al. | |
| 2010/0189829 A1 | 7/2010 | Bernaert et al. | |

FOREIGN PATENT DOCUMENTS

| | | |
|---|---|---|
| CN | 1113114 | 12/1995 |
| CN | 1113114 | 6/2009 |
| EP | 493151 | 7/1992 |
| EP | 1366672 | 12/2003 |
| EP | 1609466 | 12/2005 |
| EP | 1676606 | 7/2006 |
| EP | 1787970 | 5/2007 |
| FR | 2885050 | 4/2005 |
| FR | 2 885 050 | 11/2006 |
| JP | 2002/173435 | 6/2002 |
| JP | 2002/272376 | 9/2002 |
| WO | WO 9610404 | 4/1996 |

(Continued)

OTHER PUBLICATIONS

Bernaert, Herwig et al., "Chocolate is good for you. The sweet truth about chocolate", Agro Food Industry Hi-Tech, 2006, vol. 17, No. 1, pp. 22-23.
Bernaert, Herwig et al., "The nutritional aspects of chocolate", Food Science and Technology Today, 2006, vol. 20, No. 4, pp. 17, 19-20.
Eteng, M. et al., "Theobromine Rich Cocoa Powder Induces Weight Loss and Changes in Lipid Profile of Obese Wistar Rats", Discovery and Innovation, 2006, pp. 191-196.

(Continued)

*Primary Examiner* — Terry A McKelvey
*Assistant Examiner* — Randall Winston
(74) *Attorney, Agent, or Firm* — Hoxie & Associates LLC

(57) ABSTRACT

A cocoa extract obtainable by the extraction of non-defatted cocoa beans which have not been fermented or have been allowed to ferment for no more than three days, having a polyphenol content of more than 25% by weight, may be used in the treatment or alleviation of obesity.

23 Claims, 1 Drawing Sheet

(56) References Cited

FOREIGN PATENT DOCUMENTS

| | | |
|---|---|---|
| WO | WO 9802165 | 1/1998 |
| WO | WO 98/09533 | 3/1998 |
| WO | WO 9809533 | 3/1998 |
| WO | WO 9934675 | 7/1999 |
| WO | WO 9965322 | 12/1999 |
| WO | WO 02/14251 | 2/2002 |
| WO | WO 0214251 | 2/2002 |
| WO | WO 03079998 | 10/2003 |
| WO | WO 2004087181 | 10/2004 |
| WO | WO 2004103334 | 12/2004 |
| WO | WO 2006086764 | 8/2006 |
| WO | WO 2006117465 | 11/2006 |
| WO | WO 2006117466 | 11/2006 |
| WO | WO 2006/128259 | 12/2006 |
| WO | WO 2006128259 | 12/2006 |
| WO | WO 2007/002851 | 1/2007 |
| WO | WO 2007042745 | 4/2007 |
| WO | WO 2007061873 | 5/2007 |
| WO | WO 2007063563 | 6/2007 |
| WO | WO 2007082703 | 7/2007 |
| WO | WO 2008/131911 | 11/2008 |
| WO | WO 2008/131912 | 11/2008 |

OTHER PUBLICATIONS

Matsui, N. et al., "Ingested cocoa can prevent high-fat diet-induced obesity by regulating the expression of genes for fatty acid metabolism", Nutrition, 2005, vol. 21, pp. 594-601.

Thomson Scientific, London, GB; AN, 1997-403398, XP002486401.

Bernaert, H., The Nutritional Aspects of Chocolate, Food Science and Technology Today, 2006, pp. 17,19-20, vol. 20, No. 4.

Eteng, M.U., et al., Theobromine Rich Cocoa Powder Induces Weight Loss and Changes in Lipid Profile of Obese Wistar Rats, Discovery and Innovation, 2006, pp. 191-196.

Bernaert, H., Chocolate is Good for You, The Sweet Truth About Chocolate, Agro Food Industry Hi-Tech, 2006, vol. 17, No. 1, pp. 22-23.

Matsui, N., et al., Ingested Cocoa Can Prevent High-Fat Diet-Induced Obesity by Regulating the Expression of Genes for Fatty Acid Metabolism, Nutrition, 2005, pp. 594-601, vol. 21, No. 5.

Vanina, Y, et al., Body Weight Changes Associated with Psychopharmacology, Psychiatric Services, 2002, pp. 842-847, vol. 53, No. 7.

Singleton, V.L., et al., Analysis of Total Phenols and Other Oxidation Substrates and Antioxidants by Means of Folin-Ciocalteu Reagent, Methods in Enzymology, vol. 299, pp. 152-178 (1999).

Okiyama, M., et al., Effects of Combined Administration of Diazepam and Imipramine Hydrochloride in Rats, Journal of Pharmaceutical Sciences, vol. 75, No. 11, pp. 1071-1075, (Nov. 1986).

Abe; "Nutrigenomics"; The University of Tokyo, Farumashia; vol. 42, No. 9; pp. 894-898; 2006; Abstract Only.

Caron et al; "Influence of Dibencycladine and Imipramine on the Caloric Intake and Body Weight"; Int. J. Pharmacol.; 1973; 7: 37-43.

Office Action from Japanese Application No. JP 2010-504547 dated Jul. 2, 2013; English Translation.

Office Action from Japanese Application No. JP 2010-504547 dated Mar. 5, 2013; English Translation.

Onuma et al; "Anti-Depression Activity of N-lignoseroltryptamine-related Compounds as Cocoa Components"; Journal of Japan Pharmacology Association; 2004, vol. 123, No. 1, p. 14p.

Takeda; Anti-Stresss Effect of Cacao Beans Components; Food Science, 1997; No. 228, pp. 52-56; English Abstract Only.

Takeda; "Benefit of Chocolate/Cocoa, Anti-Stress Effect of Cacao Mass Polyphenol, Evaluation by Menopausal Unidentified Complaint Model"; Food Science, 1990, No. 252, pp. 50-52; English Translation.

Takeda; "Pharmaceutical Characteristics of Cacao Mass Polyphenol, Anti-Sress Effect"; Food Science; 1998, No. 240, pp. 63-65; English Translation.

Watanabe et al; "Benefit of Chocolate/Cocoa, View and Feeling for Chocolate"; Food Science, 1999, No. 252, pp. 22-29; English Translation.

* cited by examiner

USE OF COCOA EXTRACT

CROSS REFERENCE TO RELATED APPLICATIONS

This application is a United States Application under 35 USC §371 claiming benefit of PCT/EP2008/003322 filed Apr. 24, 2008, which claims priority to U.S. Application No. 60/926,328, filed Apr. 26, 2007, and GB Application No. 0719542.3 filed Oct. 8, 2007, the contents of each of which are incorporated herein by reference.

This invention relates to a cocoa extract and to its uses. In particular, the invention relates to uses for cocoa extracts in the treatment or alleviation of obesity.

Chocolate and cocoa are popularly claimed to have a plethora of positive effects, including stimulant, relaxant, euphoriant, aphrodisiac, tonic and antidepressant properties. However, the scientific basis for these claims has been elusive. Certainly, depression may in some individuals lead to a craving for sweet foods, and people may receive a transitory uplift in mood from the pleasure of consuming chocolate or from relief of hypoglycemia due to consumption of the sugar in the chocolate. However, the various chemicals in chocolate (other than sugar) suggested to have potentially psychoactive or mood altering effects are generally not present at pharmacologically effective levels.

Cocoa for the production of chocolate is made from the dried and partially fermented seeds of the cacao tree. The harvested cacao pods are opened, the pulp and cocoa beans are removed, and the rind is discarded. The pulp and beans are then piled in heaps, placed in bins, or laid out on grates for usually 6-7 days, during which time the thick pulp liquifies as it ferments. The fermented pulp trickles away, leaving the cocoa beans behind to be collected, dried and further processed to make cocoa butter and cocoa powder. In some instances, the product is treated with alkali to reduce the acidity of the powder. Fermentation is important for the quality and flavor of the beans, which originally have a strong bitter taste. Unfermented or underfermented cocoa beans have a flavor similar to raw potatoes, are very susceptible to mildew and fungal growth, and therefore are not used in the manufacture of chocolate for food consumption. The cocoa bean without its shell is known as a "cocoa nib".

Cocoa is known to contain polyphenols and other biologically active compounds such as xanthines, including theobromine and caffeine.

Obesity is a condition in which the natural energy reserve, stored in the fatty tissue of humans and other mammals, is increased to a point where it is associated with certain health conditions or increased mortality. Although obesity is an individual clinical condition, it is increasingly viewed as a serious and growing public health problem.

Cocoa extracts containing polyphenols have been proposed for a number of uses. For example, WO 96/010404 describes cocoa extracts containing proanthocyanidins that are said to be anti-neoplastic. U.S. Pat. No. 7,122,574 discloses polyphenol-containing cocoa extracts that can be used for treating hypertension. WO 03/079998 states that cocoa extracts containing polyphenols can be used in the treatment of diseases involving defective gap junctional communication.

Actives in cocoa extracts other than polyphenols have also been used in an attempt to achieve physiological effects. For example, U.S. Pat. No. 6,927,280 discloses a cocoa albumin and its uses. U.S. Pat. No. 7,115,285 relates to a composition, comprising theobromine or a salt thereof, for suppressing appetite and cravings for substances such as nicotine, coffee, sweets or chocolate while improving energy and enhancing mood. WO 2007/042745 discloses a composition comprising chocolate which is enhanced with theobromine and reviews the active components in chocolate, stating that cocoa contains a number of chemical substances whose influence on human and/or animal physiology is not fully understood, including phenylethylamine and tyramine which act as neurotransmitters and may effect mood swing by causing an emotional high, which can be associated with a feeling of alertness and contentment.

U.S. Pat. No. 7,122,574 discloses a polyphenol-containing cocoa extract and numerous applications for it, including an effect on satiety. The extracts were made from defatted cocoa material.

WO 98/09533 describes cocoa components having enhanced levels of cocoa polyphenols. US 2004/0096566 relates to a method for obtaining cocoa bean polyphenol extracts.

US 2004/0005347 relates to a composition and method for treating several disorders including obesity, that involves the use of cocoa or one of its active components together with a dopamine D2 receptor agonist.

US 2003/0206981 describes compositions comprising dietary fibre extracted from cocoa bean husks. The compositions are stated as being useful in the treatment of metabolic disorders.

EP-A-1609466 states that a composition in tablet form comprising cinnamon leaf oil, ginger extract, oleoresin or oil, turmeric extract oil and/or oleoresin, cocoa extract, citric acid, citrus essential oils, and a white kidney bean protein fraction with alpha amylase inhibitory activity, can be used for treating overweight humans and animals. The cocoa extract contains 6% theobromine but it is not clear how it is produced.

US 2006/0210653 relates to compositions for increasing a person's natural metabolic rate. A cocoa extract is one of the many possible extracts described but there is no indication as to how it is produced.

US 2006/0204599 relates to a dietary supplement derived from Acacia for maintaining weight loss.

US 2006/0134230 discloses a weight loss composition comprising several extracts, including a cocoa extract. The cocoa extract contains theobromine but there is no indication as to how it is produced.

WO 02/14251 describes a method for obtaining cocoa bean polyphenol extracts by solvent extraction of fresh cocoa beans. The extracts have cosmetic, food and therapeutic uses and may contain increased levels of beta-sitosterol.

WO 2007/082703 relates to the use of cocoa polyphenols, which may be produced by the method described in WO 02/14251, in beer production.

FR-A-2885050 describes a slimming cosmetic and/or pharmaceutical composition comprising a cocoa extract containing polyphenols for the treatment of adipocytes of the skin.

There remains a need for compositions that are useful in the treatment or alleviation of obesity, particularly compositions that are derived from natural products. There also remains a need for compositions having these benefits that can be readily incorporated into formulations for oral consumption. For example, the compositions for incorporation into foods and beverages are desirably readily dispersible and impart a good appearance to the product, in terms of colour and/or texture.

According to the invention, there is provided a cocoa extract obtainable by the extraction of non-defatted cocoa beans which have not been fermented or have been allowed to ferment for no more than three days, having a polyphenol content of more than 25% by weight, for use in the treatment or alleviation of obesity.

In another aspect, the invention provides the use of a cocoa extract obtainable by the extraction of non-defatted cocoa beans which have not been fermented or have been allowed to ferment for no more than three days, having a polyphenol content of more than 25% by weight, in the manufacture of a medicament for use in the treatment or alleviation of obesity.

In a further aspect, the invention provides a method for the treatment or alleviation of obesity, comprising administering an effective amount of a cocoa extract obtainable by the extraction of non-defatted cocoa beans which have not been fermented or have been allowed to ferment no more than three days, having a polyphenol content of more than 25% by weight.

It has been found that the extracts according to the invention, prepared from non-defatted cocoa beans which have not been fermented or have been fermented for a short time, such as less than three days, have advantages in terms of their effect in treating obesity. This was surprising. Most of the known cocoa extracts that are asserted as having physiological effects are derived from defatted and/or fermented beans, which are often also roasted.

The extract of the invention is typically a brown-coloured, free-flowing powder. Usually, the extract will have no noticeable odour.

The extract of the invention preferably has a polyphenol content of at least 27% by weight, more preferably at least 30% by weight, even more preferably at least 40% by weight, such as at least 45% by weight. The upper limit for the polyphenol content is typically about 70% by weight. Thus, preferred amounts of polyphenol include from 30% to 70%, from 35% to 70%, from 40% to 70%, from 45% to 65% and from 45% to 60%, the percentages being by weight of the extract. The percentages of polyphenols are preferably expressed as gallic acid equivalents, according to the Folin-Ciocalteu method (e.g., as described in Singleton V L, Orthofer R, Lamuela-Raventos R M. Analysis of total phenols and other oxidation substrates and antioxidants by means of Folin-Ciocalteu reagent. Meth Enzymol 1999; 99: 152-178).

Polyphenols in the extracts of the invention typically comprise monomers and oligomers. Preferably, the extracts of the invention comprise up to 10% by weight of each of monomers, dimers, trimers, tetramers, pentamers, hexamers, heptamers, octamers, nonamers and decamers, and higher oligomers in an amount of up to 15% by weight. More preferably, extracts of the invention comprise, by weight of the extract, 5-10% monomers (preferably including at least 5% epicatechin), 5-10% dimers, 5-10% trimers, 2-8% tetramers, 2-8% pentamers, 2-8% hexamers, 0.5-5% heptamers, 0.1-4% octamers, 0.1-3% nonamers and 0.05-2% decamers, and 5-12% higher oligomers.

Extracts of the invention may contain xanthines (preferably methylxanthines), such as caffeine and theobromine. Caffeine may be present together with theobromine, typically at a weight ratio of theobromine to caffeine in the range of from 20:1 to 5:1. In one embodiment of the invention, the theobromine content is at least 5% by weight, and preferably from 5 to 11% by weight. In this embodiment, the composition preferably has a weight ratio of from 7:1 to 12:1 polyphenol:theobromine. In an alternative embodiment, the extract may be treated, for example with supercritical carbon dioxide, to lower the theobromine content and the content of other xanthines that may be present. A method for lowering the content of theobromine in extracts of this type is described in Example 2.3 of WO 2007/082703, the contents of which are incorporated herein by reference. In this alternative embodiment, the extract has a theobromine content of less than 5% by weight, such as less than 4.5% by weight, for example from 0.1 to 4% by weight.

Figure 1:
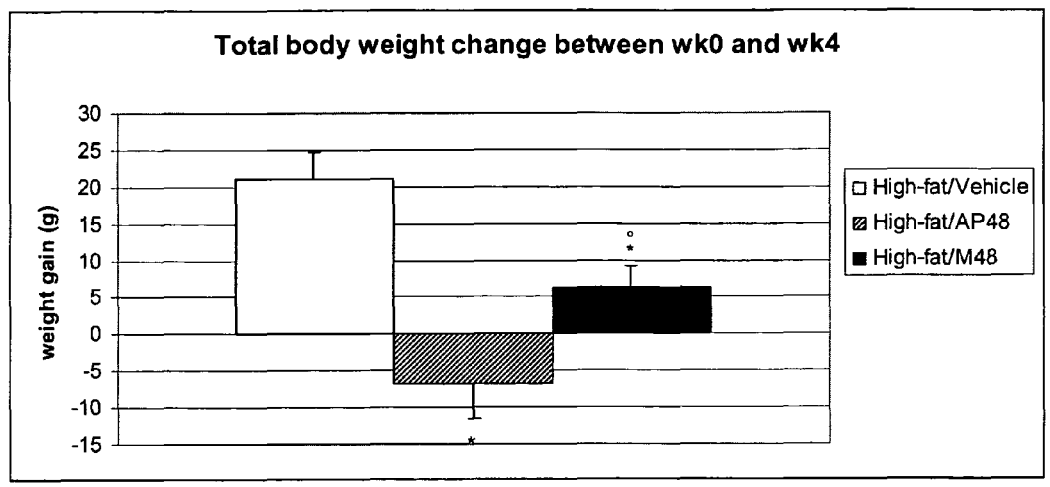
FIG. 1 depicts body weight evolution over 4 weeks (starting at wk0 and finishing at wk4) on a high-fat diet.

The extracts of the invention are prepared from cocoa beans that are non-defatted and have not been fermented or have been allowed to ferment for no more than three days. The cocoa beans will typically not have been roasted. Thus, the cocoa beans that are used as the starting material for the production of the extracts of the invention are very different from the cocoa beans that are used to produce cocoa powder and chocolate. Typically, the extracts are prepared from cocoa nibs which are deshelled cocoa beans that are unfermented and non-roasted.

The cocoa beans are preferably obtained by a process that comprises: harvesting and hulling cocoa beans; preventing fermentation of the beans or allowing the beans to ferment for no more than three days (more preferably less than two days, even more preferably less than one day) before halting the fermentation process by drying.

The fat content of the non-defatted cocoa beans, or of the cocoa nibs, that are used in the invention, is typically greater than 30% by weight, more preferably greater than 35% by weight, even more preferably greater than 40% by weight, such as greater than 45% by weight; for example, greater than 50% by weight.

Extracts of the invention are preferably obtainable by solvent extraction of the cocoa beans. The solvent is preferably selected from C1 to C6 alcohols or C1 to C6 ketones, and mixtures thereof, optionally in admixture with water, such as, for example, ethanol, acetone, 2-butanol, 2-propanol and mixtures thereof, optionally in admixture with water. A particularly preferred solvent comprises a mixture of water and acetone in a weight ratio of water:acetone of from 1:1 to 1:9. Preferably, solvent extraction is carried out using a counter current process for a time and at a temperature to achieve the desired degree of extraction, typically from one hour to 2 days at from 20 to 60° C. After extraction, the liquid solvent extract is evaporated to remove a part of the solvent and then spray dried. To improve its solubility, the extract powder is preferably agglomorated in a fluidised bed. The xanthine (and theobromine) content of the extract may be reduced by extraction with super-critical carbon dioxide after the solvent has been removed.

Processes that may be used for producing the extracts of the invention are described in WO 2007/082703 and WO 02/14251, the contents of which are incorporated herein by reference.

Extracts of the invention preferably comprise less than 2% by weight phenylethylamine.

Extracts of the invention may comprise other components derived from the cocoa beans such as protein and sugars. Typically, the extracts comprise from 15 to 40% by weight protein, such as from 20 to 30% by weight protein. The extracts may comprise from 2 to 12% by weight sugars, such as from 4 to 10% by weight sugars.

The extracts of the invention comprise cocoa fats. The term "fats" as used in this context includes lipid material in cocoa beans such as sterols, lipids and phospholipids, as well as mono-glycerides and di-glycerides. Without wishing to be bound by theory, it is believed that these one or more components of the cocoa fats contribute to the beneficial physiological effects of the extracts of the invention. Preparing the extracts of the invention from cocoa beans which have not been defatted or fermented for any substantial length of time increases the amounts of these fat components compared to extracts from defatted beans or beans that have been fermented.

Preferably, the extracts of the invention comprise from 0.1 to 10% by weight of cocoa fats, such as from 0.2 to 8%, or from 0.3 to 7%, or from 0.5 to 5%, or from 0.7 to 3%, by weight of cocoa fats. Preferably, the cocoa fats are non-triglyceride lipids.

An example of a preferred extract of the invention comprises:
(i) from 35 to 70% by weight cocoa polyphenols;
(ii) from 1 to 10% by weight xanthines;
(iii) less than 2% by weight phenylethylamine; and
(iv) from 0.1 to 10% by weight of cocoa fats.

Another extract of the invention comprises by weight 50-60% polyphenols, 7-10% theobromine, and less than 2% phenylethylamine. For example, this extract may comprise by weight 54-58% polyphenols, 8-9% theobromine, and 0.5-1.5% phenylethylamine. In these compositions, the fat content is preferably no more than 1% and/or the sugar content is no more than 3%.

One or more extracts of the invention may be admixed to form a mixed extract composition.

The extracts are used in the invention to treat or alleviate obesity (preferably in a human). The term "obesity" is used herein to refer to obese and overweight condition. These conditions may be determined by measuring body mass index, waist to hip ratio or body fat. The extracts of the invention do not rely for their action on a satiety effect or on appetite suppression or on an anti-depressive or mood enhancement effect. Instead, and without wishing to be bound by theory, it is believed that the extracts have the effect of increasing metabolism and/or the rate at which fat is burned by the subject. Therefore, the invention provides the treatment or alleviation of obesity by increasing metabolism and, in another aspect, relates to the use of the extracts for increasing metabolic rate.

Extracts and compositions of the invention preferably do not contain a dopamine D2 receptor agonist added to the cocoa extract (e.g., from a plant extract other than a cocoa extract).

The extracts of the invention are preferably formulated for oral consumption. For example, the extract may be provided as part of a foodstuff or confectionery product. Typically, the extract will be included in the foodstuff or confectionery product in an amount of from 0.1% to 50% by weight, such as from 0.5% to 10% by weight.

Foodstuffs and confectionery products include, for example, those having a fat continuous phase as well as those having a water continuous phase. Foodstuffs include foods and beverages.

Beverages include those adapted for consumption hot or cold. Beverages include one or more additives selected from sweeteners, flavouring agents, colouring agents, stabilisers and preservatives. Beverages will typically comprise from 50% to 99% water. Beverages will typically comprise the extracts of the invention dispersed and/or suspended therein. The extract of the invention may be formulated as a powder which can be converted to a beverage on the addition of water and mixing.

Foodstuffs typically comprise one or more of protein, fat and carbohydrate. Foodstuffs include dairy products and confectionery products. A preferred foodstuff comprises vegetable fat and/or cocoa butter. Particularly preferred foodstuffs include chocolate and chocolate-like products comprising cocoa solids and sugar. For example, the extracts of the invention may be included in conventional chocolate or chocolate-like products in amounts of from 0.1% to 50% by weight, such as from 0.5% to 25% by weight.

Chocolate or chocolate-like products preferably comprise one or more components selected from the group consisting of cocoa materials, sugars, sugar substitutes, milk powders, fat, emulsifier, flavouring agents and mixtures thereof.

Preferably, the cocoa materials are selected from cocoa powder, cocoa mass, cocoa liquor, cocoa butter and mixtures thereof. Milk powders include, for example, skimmed milk powder, whey powder and derivatives thereof, full cream milk powder and mixtures thereof. Suitable sugars include sucrose, fructose, glucose and dextrose and mixtures thereof (with sucrose being preferred). Sugar substitutes preferably include inulin, dextrin, isomaltulose, polydextrose and maltitol and mixtures thereof. Fats include butter fat or fractions thereof, palm oil or fractions thereof, coconut or fractions thereof, palm kernel oil or fractions thereof, liquid oils (for example, sunflower oil and/or rapeseed oil), interesterified mixtures of the above fats or fractions or hardened components thereof, or mixtures thereof. Emulsifiers include lecithin, fractionated lecithin and PGPR or mixtures thereof. Flavouring agents include vanilla and caramel or mixtures thereof.

Chocolate and chocolate-like products may comprise one or more food additives such as biscuit, nuts (whole or pieces), crispies, sponge, wafer or fruit, such as cherries, ginger and raisins or other dried fruit. These additives are normally embedded in the product.

Alternatively, the extract may be provided as a pharmaceutical composition or supplement.

Pharmaceutical compositions are preferably in the form of tablets, pills, capsules, caplets, multiparticulates including: granules, beads, pellets and micro-encapsulated particles; powders, elixirs, syrups, suspensions and solutions. Pharmaceutical compositions will comprise a pharmaceutically acceptable diluent or carrier. Pharmaceutical compositions are preferably adapted for administration parenterally (e.g., orally). Orally administrable compositions may be in solid or liquid form and may take the form of tablets, powders, suspensions and syrups. Optionally, the compositions comprise one or more flavouring and/or colouring agents. Pharmaceutically acceptable carriers suitable for use in such compositions are well known in the art of pharmacy. The pharmaceutical compositions of the invention may contain 0.1-99% by weight of the extract.

Supplements may, for example, comprise the extract in liquid form (e.g., as a solution, dispersion or suspension) and/or encapsulated in a capsule. Supplements (which term includes dietary and nutritional products) may take the form of a soft gel or a hard capsule comprising an encapsulating material, preferably selected from the group consisting of gelatin, glycerol, starch, modified starch, starch derivatives such as glucose, sucrose, lactose and fructose. The encapsulating material may optionally contain cross-linking or polymerizing agents, stabilizers, antioxidants, light absorbing agents for protecting light-sensitive fills, preservatives and the like. Preferably, the amount of the extract in the food supplements is from 1 mg to 1000 mg (such as from 50 to 500 mg).

As used herein, the term "effective amount" refers to the amount of an extract or composition which is effective, upon single or multiple dose administration to a patient, in treating obesity. An effective amount of the extracts of the invention, is in general, about 0.1 to 20 g/day, e.g., 1-10 g/day for an adult human, most preferably from 0.5 to 5 g/day. The daily dose may be administered once per day, or in divided doses. The extract can be administered orally, transdermally or rectally, preferably orally. An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The listing or discussion of an apparently prior-published document in this specification should not necessarily be taken as an acknowledgement that the document is part of the state of the art or is common general knowledge.

The following non-limiting examples illustrate the invention and do not limit its scope in any way. In the examples and throughout this specification, all percentages, parts and ratios are by weight unless indicated otherwise.

EXAMPLE 1

Evaluation of the Anti-Obesity Effect of Cocoa Polyphenol Extract in Female Sprague-Dawley Rats on a High Fat Diet Extract The extract was prepared by extraction of cocoa nibs (deshelled cocoa beans unfermented and non-roasted) in a counter-current process with the use of a 70/30 mixture of acetone/water. The liquid extract is evaporated and then spray-dried. To improve solubility, the extract powder is agglomerated in a fluidised bed.

The extract had the following composition (% by weight):

| | |
|---|---|
| Polyphenols | 47.5 |
| Ash | 4.3 |
| Xanthines | 6.9 |
| Moisture | 3.5 |
| Fat | 1.5 |
| Sugars | 6.1 |
| Proteins | 24.5 |
| Fibres | 5.5 |
| Others | 0.2 |

The polyphenol content (as % by weight of total polyphenols) was as follows:

| | |
|---|---|
| Monomers | 8.2 |
| | (7.15% epicatechin and 1.04% catechin) |
| Dimers | 7.1 |
| Trimers | 7.3 |
| Tetramers | 4.4 |
| Pentamers | 3.8 |
| Hexamers | 3.5 |
| Heptamers | 1.4 |
| Octamers | 0.9 |
| Nonamers | 1.1 |
| Decamers | 0.4 |
| Higher | 9.5 |

No gallic acid or gallic acid derivatives were detected.

Treatment

Testing was carried out using 24 female Sprague-Dawley rats. A daily dose of cocoa polyphenol extract of 48 mg/kg body weight (BW) (n=12) or a placebo (spring water 10 ml/kg BW) (n=12) was given for 4 weeks on a high fat diet (31% lard and 3% soybean oil). The cocoa polyphenolic extract (48 mg/kg BW) displayed an anti-obesity effect by limiting significantly the body weight gain of rats, without affecting food and water consumption and by significantly reducing the gain of fat mass. The effect on CPT-1 expression (enzymes) underpins the hypothesis of a higher catabolism of fat. BW at week 4 is 7% lower in the cocoa polyphenol group compared to the BW at week 4 in the placebo group.

| | Placebo | Cocoa polyphenol extract |
|---|---|---|
| BW wk 0 (g) | 283 +/− 14.1 a | 281.8 +/− 13.8 a |
| BW wk 4 (g) | 311.8 +/− 11.0 a | 288.9 +/− 13.8 b |
| TG (g) | 28.1 +/− 6.8 a | 7.2 +/− 2.4 b |
| TFI wk 0(g/kg BW) | 45 | 45 |
| TFI wk 4 (g/kg BW) | 40 | 40 |
| Water intake wk 0 (g/kg BW) | 60 | 60 |
| Water intake wk 4 (g/kg BW) | 60 | 55 |
| Fat mass difference wk 4 vs wk 0 (%) | 0.72 ± 0.25 a | 0.04 ± 0.45 b |
| CPT-1 (nmol/min/mg) | 6.03 +/− 1.02 a | 9.54 +/− 0.98 b |

TG: total gain, TFI: total feed intake, CPT-1: carnitine palmitoyltransferase, a different letter in one row indicates a statistically significant difference with $P < 0.05$

EXAMPLE 2

Comparison of Defatted and Non-Defatted Cocoa Polyphenol Extracts

A defatted polyphenolic extract was prepared as follows.

Defatted cocoa cakes were ground in a homogenizer (Waring blender) and a portion of hexane was added. The mixture was stirred for 30 minutes at room temperature and at about 400 rpm. After 30 minutes, this mixture was filtered through a glass filter type 3. The residue was recuperated and dried under high vacuum using an oil pump. This residue was extracted with another amount of hexane using the same extraction conditions. The residue was recuperated and dried under high vacuum for further extraction using acetone/water. The cocoa powder, that was recuperated on the filter after two hexane extractions and dried under high vacuum, was extracted using a mixture of acetone/water (1/1, v/v) with 0.5% acetic acid added (pH=3). This mixture was stirred for 30 minutes at room temperature and at about 400 rpm. After 30 minutes, this mixture was filtered through a glass filter type 3. The residue was recuperated and extracted with an additional amount of a mixture of acetone/water (1/1, v/v) with 0.5% acetic acid added (pH=3) using the same extraction conditions. The filtrates were combined and the solvent was removed under vacuum with a rotavapor. The remaining water fraction was lyophilized for 48 h. The extract had a polyphenol content (Folin) of 31.75%.

A cocoa polyphenolic extract of the invention was prepared from non-defatted cocoa beans generally as described in Example 1 but having a comparable polyphenol content to the extract from defatted beans.

The cocoa polyphenolic extract of the invention (referred to as AP48) and the cocoa polyphenolic extract from defatted cocoa beans (referred to as M48) were both orally administered at the dose of 48 mg/kg BW for 4 weeks to obesity induced female Sprague-Dawley rats.

Body weight and final body fat mass were determined before and after treatment and the results were as follows.

Body weight evolution over 4 weeks (starting at wk0 and finishing at wk4) on a high-fat diet is shown in the following table and the results are depicted in FIG. 1.

|  | High-fat/Vehicle (n = 12) | High-fat/AP48 (n = 12) | High-fat/M48 (n = 12) |
|---|---|---|---|
| BW wk 0 (g) | 255.5 ± 4.4 | 254.2 ± 3.2 | 254.3 ± 3.3 |
| BW wk 4 (g) | 276.6 ± 2.7 | 248.6 ± 4.5 | 260.5 ± 2.9 |
| Wk 4: Post-hoc unpaired t-test (vs. High-fat/Vehicle) | | t = 5.45 | t = 4.05 |
| Significance | | P < 0.0001 | P = 0.0005 |
| Wk 4: Post-hoc unpaired t-test (vs. High-fat/AP48) | | | t = 2.27 |
| Significance | | | P = 0.034 |

BW: body weight

Figure 2:
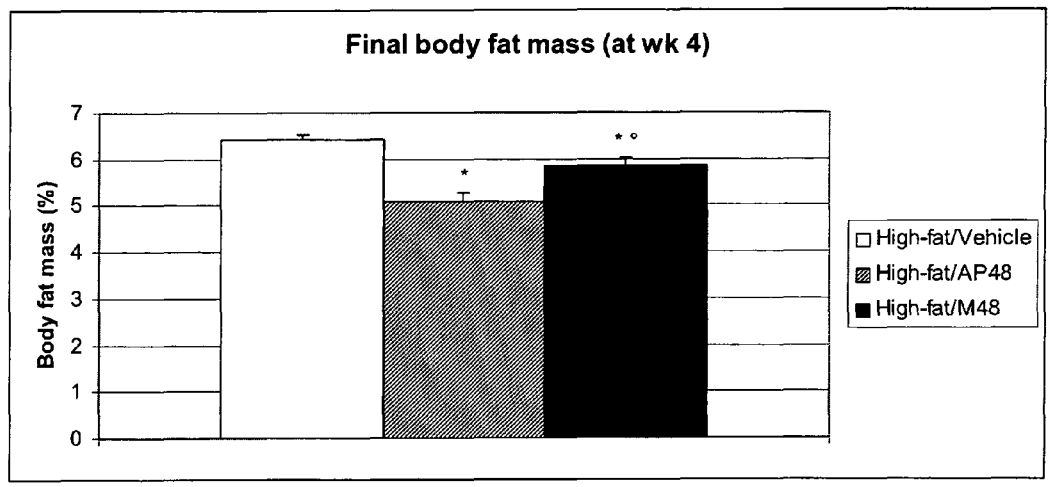
FIG. 2 depicts the results for body fat (%) evolution over 4 weeks on a high-fat diet.

The results for body fat (%) evolution over 4 weeks on a high-fat diet are shown in the following table and are depicted in FIG. 2.

|  | High-fat/Vehicle (n = 12) | High-fat/AP48 (n = 12) | High-fat/M48 (n = 12) |
|---|---|---|---|
| Fat mass wk 0 (%) | 5.55 ± 0.16 | 5.42 ± 0.13 | 5.49 ± 0.14 |
| Fat mass wk 4 (%) | 6.44 ± 0.08 | 5.09 ± 0.19 | 5.84 ± 0.17 |
| Wk 4: Post-hoc unpaired t-test (vs. | | t = 7.01 | t = 3.18 |
| Significance | | P < 0.0001 | P = 0.004 |
| Wk 4 Post-hoc unpaired t-test (vs. High-fat/AP48) | | | t = 2.97 |
| Significance | | | P = 0.008 |

Both extracts reduced the effects of induced obesity by limiting significantly the increase of body weight and by inhibiting or limiting the increase of body fat mass. Greater effects were observed with the extract of the invention in all of the parameters measured.

The invention claimed is:

1. A method for the treatment or alleviation of obesity, comprising orally administering an effective amount of a cocoa extract, to a subject in need thereof, wherein the cocoa extract is obtained by the extraction of non-defatted cocoa nibs obtained from cocoa beans which have not been fermented or have been allowed to ferment for no more than three days, having a polyphenol content of more than 25% by weight.

2. The method of claim 1 wherein said extract has a polyphenol content of at least 30% by weight.

3. The method of claim 1 wherein said extract has a polyphenol content of from 30 to 70% by weight.

4. The method of claim 1 wherein said extract has a theobromine content of at least 5% by weight.

5. The method of claim 1 wherein said extract has a theobromine content of less than 5% by weight.

6. The method of claim 1, wherein said extract is obtainable by solvent extraction of the cocoa nibs.

7. The method of claim 6, wherein the solvent is selected from C1 to C6 alcohols or ketones, and mixtures thereof, optionally in admixture with water.

8. The method of claim 7, wherein the solvent is selected from ethanol, acetone, 2-butanol, 2-propanol and mixtures thereof, optionally in admixture with water.

9. The method of claim 1, wherein the extract comprises less than 2% by weight phenylethylamine.

10. The method of claim 1, wherein said extract comprises from 0.1 to 10% by weight of cocoa fats.

11. The method of claim 10, wherein said extract comprises from 0.2 to 5% by weight of cocoa fats.

12. The method of claim 10, wherein the cocoa fats are non-triglyceride lipids.

13. The method of claim 1 wherein said extract comprises:
(i) from 35 to 70% by weight cocoa polyphenols;
(ii) from 1 to 10% by weight xanthines;
(iii) less than 2% by weight phenylethylamine; and
(iv) from 0.1 to 10% by weight of cocoa fats.

14. The method of claim 1, wherein said extract comprises from 15 to 40% by weight protein.

15. The method of claim 1, wherein said extract comprises from 2 to 12% by weight sugars.

16. The method of claim 1 wherein said extract is provided as part of a food or confectionery product.

17. The method of claim 1 wherein said extract is provided as a pharmaceutical composition or supplement.

18. The method of claim 1, further comprising administering a pharmaceutically acceptable diluent or carrier.

19. The method of claim 18, wherein the extract has a polyphenol content of at least 30% weight.

20. The method of claim 18 wherein the extract comprises the extract of claim 13.

21. A method for the treatment or alleviation of obesity, comprising orally administering a composition comprising an effective amount of a cocoa extract, to a subject in need thereof, wherein the cocoa extract is obtained by the extraction of non-defatted cocoa beans which have not been fermented or have been allowed to ferment for no more than three days, having a polyphenol content of more than 25% by weight, wherein the composition does not comprise a dopamine D2 receptor agonist.

22. A method for the treatment or alleviation of obesity, comprising orally administering an effective amount of a cocoa extract, to a subject in need thereof, wherein the cocoa extract is obtained by the extraction of non-defatted cocoa beans with a mixture of acetone and water in a weight ratio of water: acetone of from 1:1 to 1:9 which have not been fermented or have been allowed to ferment for no more than three days, having a polyphenol content of more than 25% by weight.

23. The method of claim 1, wherein the cocoa extract is spray-dried.

* * * * *

UNITED STATES PATENT AND TRADEMARK OFFICE
CERTIFICATE OF CORRECTION

PATENT NO.        : 8,709,503 B2                                           Page 1 of 1
APPLICATION NO. : 12/597569
DATED             : April 29, 2014
INVENTOR(S)       : Bernaert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 176 days.

Signed and Sealed this
Twenty-ninth Day of September, 2015

Michelle K. Lee
*Director of the United States Patent and Trademark Office*